United States Patent [19]

Nougaret

[11] 4,291,016

[45] Sep. 22, 1981

[54] ENTERIC COATED MIXTURE OF 4-(2-HYDROXY-3-ISOPROPYLAMINO-PROPOXY) INDOLE AND SODIUM LAURYL SULPHATE

[75] Inventor: Jean-Pierre Nougaret, St. Louis, France

[73] Assignee: Sandoz Ltd., Basel, Switzerland

[21] Appl. No.: 107,167

[22] Filed: Dec. 26, 1979

Related U.S. Application Data

[63] Continuation of Ser. No. 36,690, May 7, 1979, abandoned, which is a continuation of Ser. No. 950,155, Oct. 10, 1978, abandoned, which is a continuation-in-part of Ser. No. 910,824, May 30, 1978, abandoned, which is a continuation of Ser. No. 818,092, Jul. 22, 1977, abandoned.

[30] Foreign Application Priority Data

Jul. 27, 1976 [CH] Switzerland ............... 9588/76
Oct. 14, 1977 [CH] Switzerland ............... 12585/77

[51] Int. Cl.$^3$ .................... A61K 9/36; A61K 9/62; A61K 31/405

[52] U.S. Cl. ..................... 424/35; 424/19; 424/274

[58] Field of Search ............... 424/19–22, 424/32–38, 274

[56] References Cited

U.S. PATENT DOCUMENTS

| | | | |
|---|---|---|---|
| 3,148,124 | 9/1964 | Gaunt | 167/82 |
| 3,907,983 | 9/1975 | Seth | 424/35 |
| 4,001,390 | 1/1977 | Ohno | 424/35 |
| 4,017,647 | 4/1977 | Ohno | 424/35 |

FOREIGN PATENT DOCUMENTS 1301849 1/1973 United Kingdom .

Primary Examiner—Shep K. Rose
Attorney, Agent, or Firm—Gerald D. Sharkin; Robert S. Honor; Walter F. Jewell

[57] ABSTRACT

The present invention provides a pharmaceutical composition for controlled release of 4-(2-hydroxy-3-isopropylamino-propoxy) indole in the intestinal tract, admixed with sodium lauryl sulphate, and enteric coated.

10 Claims, No Drawings

ENTERIC COATED MIXTURE OF 4-(2-HYDROXY-3-ISOPROPYLAMINO-PROPOXY) INDOLE AND SODIUM LAURYL SULPHATE

This is a continuation of application Ser. No. 36,690, filed May 7, 1979, now abandoned which in turn is a continuation of application Ser. No. 950,155, filed Oct. 10, 1978, now abandoned which in turn is a continuation-in-part of Ser. No. 910,824, filed May 30, 1978, now abandoned, which in turn is a continuation of Ser. No. 818,092, filed July 22, 1977, now abandoned.

The present invention provides a pharmaceutical composition comprising a mixture of (i) a pharmacologically active agent selected from the group of arylalkanolamines and aryloxyalkanolamines, and (ii) a physiologically tolerable anionic surfactant selected from the group of mono-sulphuric acid esters of higher fatty alcohols.

Thus, we have found that the use of component (ii) advantageously increases the enteral absorption of component (i) in the intestines.

The compositions of the invention may suitably be in final form for the controlled release of the active agent in the intestinal tract.

The pharmaceutical compositions according to the invention are particularly suitable for the administration of cardiac and circulatory agents, e.g. β-adrenoceptor blocking agents and anti-arrhythmic agents.

Such agents are well-known in the art. Aryl may be, for example, of up to 10 carbon atoms, e.g. phenyl or naphthyl, and may contain one or two heteroatoms, e.g. nitrogen as in indolyl or nitrogen and sulphur as in thiazolyl. The aryl moiety may also have one or two ring substituents, e.g. acetyl, allyl, allyloxy, aminocarbonylmethyl, cyano, methyl, chloro, methoxy, methoxyethyl, amido, hydroxy, nitro, propinyloxy, ($C_{1-4}$)alkanoylamino, methylsulfamoyl, morpholino, methylthio, and tetrahydrofurylmethyloxy substituents.

The aryl moiety may also have an alkyl chain between two adjacent carbon atoms thereby forming a saturated ring. For example, the aryl moiety nucleus may be tetralone or tetraline.

The amino moiety conveniently has a branched chain alkyl substituent of 3 to 8 carbon atoms, e.g. isopropyl or tert.-butyl.

The alkanolamine moiety is conveniently a 2-hydroxy-3-alkylaminopropyl moiety.

Examples of arylalkanolamines are:
Butidrine
Butoxamine
Dichlorisoproterenol
Labetalol
Nifenalol
Sotalol Examples of aryloxyalkanolamines are:
Acebutolol
Alprenolol
Atenolol
Bufetolol
Bunitrolol
Bunolol
Bupranolol
Metoprolol
Nadoxolol
Oxprenolol
Pargolol
Practolol
Procinolol
Propranolol
Talinolol
Timolol
Tiprenolol
Tolamolol
Toliprolol
Trimepranol Especially interesting compounds are: 4-(2-hydroxy-3-isopropylaminopropoxy)indole (Pindolol) 4-(2-hydroxy-3-isopropylaminopropoxyl)-2-methylindole, and other compounds which have a poor solubility in juices of the intestinal tract.

The active agent may be in pharmaceutically acceptable acid addition salt form. Conveniently, however, the active agent is in free base form.

The surfactant preferably has a hydrophilic-lipophilic balance value (HLB group number) of from about 35 to about 45 [HLB group numbers are well-known in the art, see for example Pharm. Act. Helv. 44, 9 (1969) and H. P. Fiedler, Lexikon der Hilfstoffe für Pharmazie, Kosmetik und angrenzende Gebiete, page 263, Editio Cantor KG., 1971].

Additionally, the surfactant preferably has a critical micelle concentration (CMC) of from about $10^{-2}$ to about $10^{-3}$.

Preferred surfactants have a high dissociation constant and may produce stable complexes with the active agent in strongly acidic media. These complexes should preferably be capable of dissolving very slowly at a pH value of below three, e.g. in gastric juices, but dissolving quickly as the pH value changes from 3 to 7.5, particularly above 5, e.g. in the intestinal juices.

The exact choice of surfactant will naturally depend on inter alia its compatibility with the active agent used, e.g. on molecular size and shape, and basicity and other pharmaceutical diluents and carriers that may be present. For example, surfactants should be avoided that form stable, insoluble precipitation products with the active agent at pH values of 5 or more.

The higher fatty alcohols may have a straight or branched chain and may contain alicyclic and/or aromatic moieties. Preferably the alcohol is a primary alcohol and has from 8 to 18 carbon atoms, especially from 12 to 14 carbon atoms.

If desired, the alcohol may be an ethoxylated fatty alcohol containing, per mole, about one to about 5 moles, and preferable 1 to 3 moles, of ethylene oxide moieties. A preferred embodiment has 2.5 moles of ethylene oxide moieties per mole of surfactant.

It is preferred to use the surfactant in the form of a salt. Preferred salt forms are those which are soluble in water including those which are readily finely in water dispersible, especially alkaline earth metal salts, e.g. a magnesium salt, organic amine salts, e.g. a triethanolamine salt, or an ammonium salt. Especially preferred, however, are the alkali methal salts, e.g. a sodium salt.

The preferred surfactant, at least for use with the indole derivatives mentioned above, is sodium lauryl monosulphate.

Naturally, if desired, more than one surfactant may be used.

The weight ratio of surfactant to active agent used, and total amount of surfactant used, will naturally depend on inter alia the chemical and physical properties of the surfactant, the type and amount of the active agent and other pharmaceutical diluents and carriers present, and the desired duration of release of active agent in the intestinal tract.

In particular, the upper limit of the weight ratio of surfactant to active agent and of the total amount of surfactant used will, of course, depend on the physiological acceptability and compatibility of the surfactant (or surfactants if more than one is present) and also the planned duration of administration and frequency of administration.

The weight ratio of surfactant to active agent in the mixture may be from about 0.2:1 to about 2:1, preferably from about 0.3:1 to about 1:1.

In particular, when the surfactant is a salt form of a monosulphuric acid ester of an alkanol, e.g. sodium lauryl sulphate, and the active agent a preferred indolyl derivative mentioned above, the preferred weight ratio of surfactant to active agent is from about 0.25:1 to about 1:1, especially from about 0.4:1 to about 0.7:1.

Further physiologically acceptable material besides the surfactant may be present. Thus, solid pharmaceutical binders and diluents may be chosen so as to afford an evenly distributed release of active material over a long period of time. Preferred binders and diluents contribute towards the formation of a matrix in the digestive tract, and are substantially resistant to, or only slowly attacked by, the intestinal juices. Examples of such binders and diluents include those insoluble in intestinal juices, e.g. physiologically acceptable calcium salts, such as calcium sulphate or calcium hydrogen phosphate dihydrate; cellulose derivatives, such as ethyl cellulose; synthetic polymers, such as polyvinyl acetate, polyvinyl chloride; and copolymers of vinyl pyrrolidone and vinyl acetate; or natural, synthetic and semi-synthetic fats, e.g. mono-, di- or tri-glycerides of palmitic and stearic acids; hydrogenated castor oil and wax; and higher fatty alcohols, e.g. cetyl stearyl alcohol DAB 7.

Alternatively, the binders and diluents may be soluble in intestinal juices, e.g. physiologically acceptable:
lactose, mannitol and other sugars;
polyvinylpyrrolidone; and
polyethylene glycols.

"Soluble" herein also covers physiologically acceptable material which is easily dispersible in the intestinal juices.

Further physiologically acceptable material may be present, e.g. flow agents such as talc and magnesium stearate.

Conveniently, the physiologically acceptable material comprises a mixture of, on the one hand, material insoluble in intestinal juices and, on the other hand, material soluble in intestinal juices. The weight ratio of insoluble material to soluble material will naturally very depending on, inter alia, the amount and physical and chemical properties of the active agent and surfactant used and, additionally, on the extent of delay desired in the release of the active agent.

If the mixture is administered in a finished form such that it is delivered to the intestines substantially intact and then becomes rapidly exposed to the intestinal juices, and release of active agent is desired to be between 40 and 80%, e.g. 50%, throughout the intestines distributed evenly over 1 to 7 hours, in general a suitable weight ratio of insoluble material (e.g. insoluble binders, matrix substances, diluents and flow agents) to soluble material [e.g. soluble binders, diluents and surfactants including component (ii)] may be from about 1:5 to about 1:0.3.

In particular, when the active agent is an indolyl derivative mentioned above, and the surfactant is sodium lauryl sulphate, a ratio of insoluble material to soluble material of from about 1:3 to about 1:1.5 is suitable in order to attain about a 40% release of active agent in the intestines distributed evenly over 1 to 4 hours.

In an especially preferred embodiment of the invention, the mixture of active agent (i) and surfactant (ii) is a medicament core coated with a physiologically acceptable film which is resistant to gastric juices but breaks down in intestinal juices.

The choice of film-forming material and its thickness will, of course, depend on, inter alia, the active agent, the surfactant and the solubility of any active agent-surfactant complex. In general, it is suitably a polymer. Such polymer may be selected such that the film dissolves at a pH value of from 5 to 8, preferably from 5 to 7, in the digestive tract in about ¼ to 2 hours, preferably in ½ to 1 hour. Preferably the film does not dissolve for at least 3 hours in artificial (U.S.P.) gastric juices at a pH value of less than 5.

Such films may be selected from known macromolecular polymers used for the production of unit dosage forms resistant to gastric juices but soluble in the small intestine. Suitable polymers are listed in e.g. Hagers Handbuch der pharmazeutischen Praxis, 4th edition, Vol. 7a, pages 739 to 742 and 776 to 778 (Springer Verlag, 1971) and Remington's Pharmaceutical Sciences, 13th edition, pages 1689 to 1691 (Mack Publ. Co., 1970), e.g. cellulose ester derivatives, acrylic resins, such as methylacrylate copolymers and copolymers of maleic acid and phthalic acid derivatives.

The preferred films are made from cellulose acetate phthalate; copolymers derived from methylacrylic acid and esters thereof, containing at least 40% methylacrylic acid; and especially hydroxypropyl methylcellulose phthalate.

The thickness of the film may depend on the degree of permeability of the film to water and acids. Preferably the thickness of the film layer is from about 5 to about 100 $\mu$m and, especially from about 20 to about 80 $\mu$m. In general, however, the weight of the film should not exceed 15% of the medicament core coated, and preferably is from 3 to 10% of the medicament core coated.

The film may surround a plurality of discrete pellets or granules each containing active agent (i) and surfactant (ii) all embedded in at least one pharmaceutical carrier or diluent. Alternatively, the film may surround a core having active agent (i) and surfactant (ii) dispersed homogenously throughout.

It is preferred to formulate a unit dosage form which, additionally, releases active agent (i) in the acid gastric juices from an outer medicament layer containing such active agent and pharmaceutical carriers or diluents soluble in gastric juices. The active agent may be rapidly absorbed through the stomach walls so that an initial high concentration of active agent in the blood is quickly reached. The level of the active agent in the blood may then be maintained by the delayed and sustained release of active agent from the core in the more alkaline juices of the intestines.

Thus, for example, the film coating may be covered by such a medicament layer.

The weight ratio of arylalkanolamine or aryloxyalkanolamine in the medicament core covered by the film to that in the medicament layer outside the film may be, for example, from about 0.75:1 to 1.25:1, e.g. 1:1.

If desired other pharmacologically active agents can be present, particularly in the outer medicament layer when used. Such agents which come into consideration are those influencing the heart and circulatory functions such as anti-hypertensives, diuretics, α-blockers, etc., particularly long acting diuretics. Thus, an aryloxyalkanolamine, such as 4-(2-hydroxy-3-isopropylaminopropoxy)indole, may be combined with a long acting diuretic, e.g. 2-methyl-3-o-tolyl-6-sulphamyl-7-chloro-1,2,3,4-tetrahydro-4-(3H)-quinazolinone or a pharmaceutically acceptable salt form thereof, for example both being present in an outer medicament layer and the former being present also in the medicament core.

The outer layer may comprise a plurality of discrete granules or pellets each containing active agent (or agents) embedded in at least one pharmaceutical carrier or diluent soluble in gastric juices. The outer layer may also surround a plurality of film-coated medicament cores. Preferably, however, the outer layer surrounds only one film coated medicament core.

Conveniently, the weight of surfactant present is from about 1 to about 30%, preferably from 1 to 10%, of the pharmaceutical composition or the medicament core, if one is present.

When the pharmaceutical composition is in unit dosage form, in general the amount of surfactant in total is less than 50 mg.

The compositions of the invention can be prepared in conventional manner. Thus, for example, component (i) can be admixed with component (ii), e.g. by pelleting or granulating the mixture using conventional wet or dry granulating techniques and compressing the resultant pellets or granules together to form a tablet core, or alternatively compressing directly without granulating or pelleting, and formulating into a suitable galenical form.

As already indicated, a preferred embodiment is where the mixture is surrounded by a film which is resistant to gastric juices but breaks down in intestinal juices. Such film may be applied to the mixture of components (i) and (ii) in conventional manner, e.g. from a solution thereof at from 10° to 60° C.

The following Examples illustrate the invention.

The materials used in the Examples are all conventional materials used in the galenic art. In particular:
Hydroxypropyl methylcellulose phthalate is e.g. HPMCP HP50 (Registered Trade Mark) obtainable from Shinetsu Chem. Co., Tokyo;
Ethylcellulose is e.g. Ethocel N (Registered Trade Mark) 7 cps obtainable from Dow Chemical Co., Midland, Mich., U.S.A.;
Polyvinylpyrrolidone/polyvinyl acetate is a macrocopolymer of vinylpyrrolidone and vinyl acetate (mole ratio 6:4), known as Luviskol VA 64, obtainable from BASF, Ludwigshafen, W. Germany;
Microcrystalline cellulose is e.g. Avicel (Registered Trade Mark) obtainable from FMC Corp., Marcus Hook, Palo Alto, U.S.A.;
Polyvinylpyrrolidone is e.g. Kollidon 90 (Registered Trade Mark) obtainable from BASF, Ludwigshafen.

The palmate/stearic acid triglyceride mixture is e.g. Precirol (Registered Trade Mark) obtainable from Establissements Gattefossé, St. Priest, France; Hydrogenated castor oil is e.g. Cutina HR (Registered Trade Mark) obtainable from Henkel, Düsseldorf, W. Germany.

EXAMPLE 1

Retard Mantle Tablet

| Component | Composition (mg/tablet) |
|---|---|
| Core | |
| Active agent | |
| 4-(2-Hydroxy-3-isopropylamino-propoxy)-indole | 5.0 |
| Surfactant | |
| Sodium lauryl sulphate[2] | 2.5 |
| Pharmaceutical binders and diluents | |
| Ethylcellulose[1] | 4.5 |
| Microcrystalline cellulose[1] | 7.0 |
| Mannitol[2] | 27.5 |
| Polyvinylpyrrolidone-polyvinyl-acetate[1] | 2.5 |
| Flow agents | |
| Talc[1] | 0.5 |
| Magnesium stearate[1] | 0.5 |
| | 50.0 mg |
| Film | |
| Hydroxypropyl methylcellulose phthalate | 3.0 |
| Medicament layer | |
| Active agent | |
| 4-(2-hydroxy-3-isopropylaminopropoxy)indole | 5.0 |
| Pharmaceutical binders and diluents and flow agents | |
| Talc | 7.9 |
| Microcrystalline cellulose | 27.5 |
| Magnesium stearate | 1.3 |
| Mannitol | 110.1 |
| Polyvinylpyrrolidone | 5.2 |
| | 157.0 |
| Total tablet weight | 210 mg. |

[1] = insoluble material and/or matrix substances
[2] = soluble material

Production

The components of the core are mixed, granulated and pressed into tablet cores using a 5 mm diameter domed tablet die.

The tablet cores are then coated by spraying with a 10% (w/v) solution of hydroxypropyl methylcellulose in ethanol/acetone (1:1 v/v). The outer medicament layer is then applied in conventional manner, by mixing the active agent for the outer layer with the other components of the outer layer except for the lubricants (talc and magnesium stearate) granulating the moist components, adding the lubricants and finally pressing the granulates together with the film coated medicament cores into tablets.

In analogous manner to that described in Example 1 mantle tablets with the core compositions (50 mg) given below in the table may be obtained.

The cores are then coated with hydroxypropyl methylcellulose phthalate film (3 mg/tablet) and a medicament layer (157 mg/tablet) as described in Example 1.

| % by weight Example No. | 1A | 1B | 1C | 1D | 1E | 1F | 1G | 1H | 1I | 1J | 1K | 1L | 1M | 1N | 1O | 1P | 1Q | 1R |
|---|---|---|---|---|---|---|---|---|---|---|---|---|---|---|---|---|---|---|
| Component | | | | | | | | | | | | | | | | | | |
| Active agent | | | | | | | | | | | | | | | | | | |
| 4-(2-hydroxy-3-isopropyl-aminopropoxy)indole | 10 | 10 | 10 | 10 | 10 | 10 | 10 | 10 | 10 | 10 | 10 | 10 | 10 | 10 | 5 | 5 | 20 | 20 |
| Surfactant | | | | | | | | | | | | | | | | | | |
| Sodium lauryl sulphate[2] | 5 | 5 | 5 | 5 | 5 | 5 | 5 | 5 | 5 | 5 | 5 | 5 | 5 | 5 | 2.5 | 2.5 | 10 | 10 |
| Binders and diluents | | | | | | | | | | | | | | | | | | |
| Ethylcellulose[1] | 9 | 10 | 9 | 9 | 9 | 11 | 9 | 11 | 9 | 11 | | 9 | 11 | 11 | 9 | 7 | 12 | 9 |
| Microcrystalline cellulose[1] | 14 | | 10 | | | | | 10 | | 12 | 13 | 13 | | 12 | 14 | | 10 | |
| Mono-, di- and triglyceride mixture of palmitic and stearic acids[1] | | | | | | | | | 15 | | | | | | | | | |
| Hydrogenated castor oil[1] | | | 12 | | | | | | 12 | | | | | | | 7 | | 10 |
| Calcium hydrogen phosphate dihydrate[1] | | | | | 10 | 12 | | | | | | | 12 | | | | | |
| Binders and diluents | | | | | | | | | | | | | | | | | | |
| Mannitol[2] | 55 | 55 | 55 | 55 | 55 | 55 | 55 | 55 | 55 | 55 | 55 | 61 | 55 | 55 | 60 | 62 | 41 | 44 |
| Polyvinylpyrrolidone-polyvinylacetate[1] | 5 | | 5 | 7 | 5 | 3 | 3 | 3 | | 3 | 5 | | 5 | 5 | 7.5 | 14.5 | 5 | 5 |
| Polyethylene glycol 4000 DAB7 W. Germany[2] | | 14 | | | | | | | | | | | | | | | | |
| Polyethylene glycol 6000 DAB7 W. Germany[2] | | | | | | 10 | | | | | | | | | | | | |
| Flow agents | | | | | | | | | | | | | | | | | | |
| Talc[1] | 1 | 5 | 5 | 1 | 5 | 5 | 5 | 5 | 5 | 1 | 1 | 1 | 1 | 1 | 1 | 1 | 1 | 1 |
| Magnesium stearate[1] | 1 | 1 | 1 | 1 | 1 | 1 | 1 | 1 | 1 | 1 | 1 | 1 | 1 | 1 | 1 | 1 | 1 | 1 |

[1] = insoluble physiologically acceptable agents and/or matrix substances
[2] = soluble physiologically acceptable agents Following the procedure used in Examples 1 and 1A to 1R, the active agent, 4-(2-hydroxy-3-isopropylaminopropoxy)indole may be replaced by an equivalent amount of an arylalkanolamine or aryloxyalkanolamine specifically mentioned above.

EXAMPLE 2

Retard Mantle Tablets

This is prepared in analogous manner to that described in Example 1.

| Core Component | Composition (mg/tablet) |
|---|---|
| Active Agent | |
| 4-(2-Hydroxy-3-isopropylamino-propoxy)-indole | 10 |
| Surfactant | |
| Sodium lauryl sulphate[2] | 5 |
| Pharmaceutical binders and diluents | |
| Ethylcellulose[1] | 9 |
| Microcrystalline cellulose[1] | 14 |
| Mannitol[2] | 55 |
| Polyvinylpyrrolidone-polyvinyl-acetate[1] | 5 |
| Flow agents | |
| Talc[1] | 1 |
| Magnesium stearate[1] | 1 |
| Film | |
| Hydroxypropyl methylcellulose phthalate | 10 |
| Medicament Layer | |
| Active Agent | |
| 4-(2-Hydroxy-3-isopropylamino-propoxy)-indole | 15 |
| Pharmaceutical Binders and Diluents and Flow Agents | |
| Starch | 30 |
| Microcrystalline cellulose | 253 |
| Silicic acid | 0.5 |
| Magnesium stearate | 1.5 |
| Total tablet weight | 460 mg. |

[1] = insoluble material
[2] = soluble material

EXAMPLE 3

Retard Mantle Tablets

This is prepared in analogous manner to that described in Example 1.

| Core Component | Composition (mg/tablet) |
|---|---|
| Active Agent | |
| 4-(2-Hydroxy-3-isopropylamino-propoxy)-indole | 15 |
| Surfactant | |
| Sodium lauryl sulphate[2] | 7.5 |
| Pharmaceutical binders and diluents | |
| Ethylcellulose[1] | 21 |
| Dicalciumphosphate dihydrate | 13.5 |
| Mannitol[2] | 82.5 |
| Polyvinylpyrrolidone-polyvinyl-acetate[1] | 7.5 |
| Flow Agents | |
| Talc[1] | 1.5 |
| Magnesium stearate[1] | 1.5 |
| Film | |
| Hydroxypropyl methylcellulose phthalate | 6.0 |
| Medicament layer | |

-continued

| Core | |
|---|---|
| Component | Composition (mg/tablet) |
| Active agent | |
| 4-(2-hydroxy-3-isopropylamino-propoxy)indole | 10.0 |
| Pharmaceutical binders and diluents and flow agents | |
| Starch | 20.0 |
| Microcrystalline cellulose | 168.6 |
| Silicic acid | 0.4 |
| Magnesium stearate | 1.0 |
| Total tablet weight | 306.0 mg. |

(1) = insoluble material
(2) = soluble material

I claim:

1. A pharmaceutical composition having a medicament matrix core comprising a mixture of 4-(2-hydroxy-3-isopropylaminopropoxy)indole, and sodium lauryl sulphate, and a physiologically acceptable film which is resistant to gastric juices and breaks down at pH of 5 or more coating the mixture.

2. A composition according to claim 1 in final form adapted for controlled release of the active agent in the intestinal tract.

3. A composition according to claim 1 wherein the film is made from hydroxypropyl methylcellulose phthalate.

4. A composition according to claim 1 wherein the film thickness is from 5 to 100 μm.

5. A composition according to claim 1 wherein the film is covered by a medicament layer of 4-(2-hydroxy-3-isopropylaminopropoxy)indole.

6. A composition according to claim 5 wherein the weight ratio of 4-(2-hydroxy-3-isopropylaminopropoxy)indole in the medicament core covered by the film to that in the medicament layer outside the film is from 0.75:1 to 1.25:1.

7. A composition according to claim 2 in unit dosage form and containing less than 50 mg of sodium lauryl sulphate.

8. A composition according to claim 1 wherein the weight ratio of sodium lauryl sulphate to 4-(2-hydroxy-3-isopropylaminopropoxy) indole in the mixture is from 0.2:1 to 2:1.

9. A composition according to claim 8 wherein the weight ratio is from 0.3:1 to 1:1.

10. A method of increasing the enteral absorption of 4-(2-hydroxy-3-isopropylaminopropoxy)indole which comprises enterally administering the pharmaceutical composition of claim 1.

* * * * *